United States Patent [19]
Order

[11] Patent Number: 6,074,626
[45] Date of Patent: Jun. 13, 2000

[54] RADIOACTIVE CISPLATIN IN THE TREATMENT OF CANCER

[75] Inventor: Stanley E. Order, Old Westbury, N.Y.

[73] Assignee: Molecular Radiation Management, Inc., Garden City, N.J.

[21] Appl. No.: 09/272,549

[22] Filed: Mar. 19, 1999

Related U.S. Application Data

[60] Provisional application No. 60/078,818, Mar. 20, 1998.
[51] Int. Cl.⁷ .......................... A61K 51/00; A61M 36/14
[52] U.S. Cl. ........................ 424/1.61; 424/1.11; 424/649
[58] Field of Search .................................. 424/1.11, 1.61, 424/649

[56] References Cited

U.S. PATENT DOCUMENTS

| | | | |
|---|---|---|---|
| 4,322,391 | 3/1982 | Kaplan et al. | 423/209 |
| 4,451,447 | 5/1984 | Kaplan et al. | 424/131 |
| 4,536,386 | 8/1985 | Keenan | 424/10 |
| 4,889,724 | 12/1989 | Kasan et al. | 424/649 |
| 5,340,565 | 8/1994 | Prio | 424/10 |
| 5,484,612 | 1/1996 | Brown | 424/649 |
| 5,844,001 | 12/1998 | McClay et al. | 514/648 |

OTHER PUBLICATIONS

Dox et al, The Harper Collins Illustrated Medical Dictionary, pp. 12, 27, & 360, 1993.
The Merck Index, pp. 361 & 1196, 1989.

*Primary Examiner*—Dameron Jones
*Attorney, Agent, or Firm*—Caesar, Rivise, Bernstein, Cohen & Pokotilow, Ltd.

[57] ABSTRACT

Background: Between 1991 and 1997 sixty-seven patients with non-resectable hepatoma were treated with hepatic artery infusions (HAI) of cisplatinum. Patients were divided into groups for analysis based on alpha-fetoprotein elevation (AFP+) or no elevation (AFP−), hepatitis B/C status, the presence or absence of extra-hepatic metastases and primary treatment at our facility or initial therapy elsewhere.

Methods: Forty-four patients received an initial course of 21–24 Gy whole liver external radiation with cisplatinum 50 mg/m² IV on days 1 and 8 of radiation. Twenty-three patients did not receive external radiation and received HAI cisplatinum only. All patients were then treated with HAI cisplatinum at 50 mg/m² on a monthly basis. The rationale for the advantage to HAI cisplatinum was evaluated by giving a tracer dose of radioactive $^{195m}$cisplatinum for quantitative determinations by the intra-arterial route in six patients.

Results: A 50% overall response rate was seen, as judged by a 50% reduction in tumor diameter or a 50% reduction in AFP titer. Monthly HAI cisplatinum at 50 mg/m² was well tolerated and could be repeated indefinitely without significant toxicity. Median survival for primarily treated non-resectable hepatomas AFP(+) and AFP(−) was 12 months and 17.5 months, respectively. Statistical analysis of all patients AFP(+) versus AFP(−) revealed a log rank statistical difference in survival of P=0.007. For patients with hepatitis B or C median survival was 10.7 months regardless of AFP status. Radioactive cisplatinum given by hepatic arterial infusion provided 34–55% tumor uptake of cisplatinum.

Conclusions: Intra-arterial delivery of 50 mg/m² cisplatinum on a monthly basis is a well-tolerated regimen for patients with non-resectable hepatoma. These data suggest a baseline chemotherapy regimen against which randomized trials could be evaluated. Further, the selective uptake of cisplatinum delivered intra-arterially suggests other selective intra-arterial protocols would be of use in regional cancers treated with cisplatinum.

Keywords: Hepatoma, hepatocellular, carcinoma, cisplatin, cisplatinum, $^{195m}$cisplatinum, radioisotopes, intra-arterial.

5 Claims, No Drawings

RADIOACTIVE CISPLATIN IN THE TREATMENT OF CANCER

This application claims the benefit of the filing date of provisional application Ser. No. 60/078,818 filed on Mar. 20, 1998, the entire disclosure of which is incorporated by reference herein.

BACKGROUND OF THE INVENTION

Hepatocellular cancer that is non-resectable has had a median survival of six months when treated. A variety of chemotherapeutic agents have been given intravenously, with less-than-realistic results. During the course of investigations in hepatocellular cancer, I surprisingly discovered that intra-arterial cisplatin at 50 mg./m$^2$ caused a 50% remission in 28 patients; and, recently, in 67 patients, a 50% response. Thus, 95 patients have had a 50% remission, with median survival extended one year to 46 months depending on the classification of the tumor. In addition to these findings, the median survival rate for the worst group of hepatomas (AFP+positive) was one year greater than the six months reported from the other therapeutic regimens.

In order to discern why intra-arterial cisplatin was superior to intravenous, I created $195^m$ cisplatin, and studied the same patient intravenously and intra-arterially. When the drug was given intravenously, less than five percent deposited in the tumor. When the drug was given intra-arterially, 35 to 40 percent of the drug deposited in the tumor, as witnessed by scintigraphic scans. The cisplatin that binds on the hepatoma apparently stays there for a persistent period of time and interrupts DNA metabolism. The use of intravenous cisplatin has had less than a five-percent response rate, and the arterial route is 50 percent or greater.

Having studied the diagnostic distribution of $195^m$ cisplatin, I realized that the possibility of treating cancer with a radioactive cisplatin exists.

I have been engaged in Phase 1 dose escalation study in which 10 mCi of radioactivity, approximately 10 mg of the drug, are substituted for the cold drug in the infusion of the liver. The dose is escalated as long as there is no significant hematologic toxicity. The maximum dose we presently give of 50 mg/m$^2$ on an average person would be about 70 to 75 mg. The procedure would take the $195^m$ cisplatin and substitute it for the cold, and the patient would get both the cold cisplatin and the radioactive cisplatin. Cisplatin is also a radiation sensitizer; and, as such, the drug should amplify the therapeutic results from the radiolabeling.

The benefit to the patient would be that the non-radioactive form and the radioactive form would still behave as the drug cisplatin, since it is created radioactive by neutron bombardment and not by chemistry alteration or linkage.

Cisplatin has been used diagnostically in a variety of tumors where its direct infusion is part of the pharmacokinetics. Therapy with $195^m$ cisplatin would have use in hematoma, bladder and brain tumors, but prior to the present invention has never been proposed for this use.

A dosage range of approximately 10 mCi to 75 mCi or more, depending upon the size of the tumor, may be given in accordance with this invention for all types of solid tumor cancers and not limited to hepatomas.

Without further elaboration, the foregoing so fully illustrates my invention that others may adapt and use the invention accordingly.

INTRODUCTION

Primary liver cancer is one of the most common and lethal cancers in the world (1,2). Once considered relatively rare in the United States, the incidence of hepatocellular carcinoma is rising (3). Potentially curative resection is limited to merely 10–20% of patients at presentation due to the large size of the tumor, cirrhosis, chronic hepatitis, portal vein occlusion, bilobar and/or metastatic disease (4,5). The vast majority of patients therefore present with non-resectable disease or relapse following resection (6). Currently available treatment modalities for non-resectable hepatoma include hepatic arterial embolization (7–15), external irradiation (16–21), hormonal manipulation (22–25), systemic intravenous (26–32) or hepatic artery-delivered chemotherapy (33–39). As treatment strategies have evolved it is clear that several chemotherapeutic agents provide negligible responses when given by the intravenous route but marked clinical responses when given by hepatic artery infusion (HAI) (40). There has been no consensus regarding the most useful agents by HAI or their optimal dosage. Cisplatinum (cisdiamminedichloroplatinum or CDDP) is one of the more effective drugs available for treatment of hepatoma yet has a relatively poor response rate when given as a single drug by the intravenous route (26,29,30,34–39). In this report we provide remission and survival rates for hepatoma patients treated monthly with intra-arterial cisplatinum at 50 mg/m$^2$. Further, we evaluated the rationale for HAI of cisplatinum, by assessing tumor deposition using quantitative $^{195m}$CDDP imaging.

METHODS

Patient population: All patients were required to have histologic documentation of hepatocellular carcinoma. Pretreatment evaluation included a complete medical history and physical examination, hepatitis virus status and complete blood cell counts, biochemical survey including lactate dehydrogenase, alkaline phosphatase, BUN, creatinine, bilirubin, PT/PTT and alpha fetoprotein (AFP) level; radiographic studies including CT scans of the chest, abdomen and pelvis with volumetric reconstruction of both tumor and normal liver volumes allowed determination of percentage of liver replacement by tumor. The presence of ascites was determined using both clinical examination and imaging results. Excluded were patients with a creatinine >1.5 and/or BUN >25. All patients gave written informed consent. Prior to referral to our facility 23 patients (34%) had multiple chemotherapeutic regimens. Of the 67 patients, 44 (65%) were treated with external beam radiation to the involved liver as a component of the prescribed treatment program. Assessment of liver function was done using the modified Childs-Pugh classification (41). The American Joint Committee on Cancer staging system was used to stage tumor extent in all patients (42).

Chemoradiation: The treatment regimen has been previously described (16,21). Briefly, patients received whole liver external radiation using 10 MV photons to a total dose of 21 to 24 Gy. Treatments were given in 7 to 8 fractions of 3.0 Gy per fraction, four days per week. CT-directed treatment planning was used throughout and provided volumetric quantitation of tumor as well as normal liver volumes (43). On treatment days 1 and 8 of radiation, cisplatinum at 50 mg/m$^2$ was given intravenously with hydration and diuresis.

Intrahepatic arterial chemotherapy: The infusion was performed either with a temporary percutaneous femoral or axillary artery catheter or implanted port or pump. On the day prior to treatment the patients were instructed to take 1 to 2 liters of fluid orally. On admission, 1 liter of 5% dextrose in normal saline with 20 meq potassium was given intravenously. Utilizing a femoral or axillary artery transcutaneous approach an arteriogram of the common hepatic artery was done. Next, cisplatinum 50 mg/m² was dissolved to a concentration of 1 mg per ml of sterile water. The solution was then infused intra-arterially at a rate of 1 mg/minute. The chemotherapy was always infused into the most distal artery feeding the main mass of the tumor. Appropriate antiemetic therapy, generally Odansetron 0.15 mg/kg IV and dexamethasone 20 mg IV was administered before the cisplatinum infusion and as needed after the infusion. On discharge home patients were given an oral antiemetic regimen of Lorazepam 1 mg, every six hours, or Odansetron 8 mg every twelve hours, as needed and Dexamethasone 4 mg every six hours for one day. Patients continued monthly HAI of cisplatinum until evidence of progressive disease or death. All patients were assessable for response.

Assessment of response: Routine clinical examinations and laboratory testing were performed at monthly intervals or as clinically indicated. The defined improvements on a minimum of two CT scans and/or AFP titers obtained at least two months apart were required to delineate response. Tumor volumes were quantified by computed tomography scan volumetric analysis of the liver as previously reported (20,43). Complete remission was the disappearance of all clinical evidence of tumor for a minimum of one month. Partial remission was a decrease of 50% or more in the volume of all measurable lesions measured on contrast-enhanced CT scan or a ≧50% reduction in AFP titer. Stable disease was a <50% decrease or <25% increase in tumor volume or AFP titer. Progressive disease was the increase of at least 25% in the tumor volume of all measurable lesions on CT scan or by AFP titer. Toxicity was assessed monthly during HAI therapy using RTOG criteria (44) with scores ≧3 considered to be major toxicities.

Radioactive $^{195m}$Cisplatinum

The rationale for HAI cisplatinum was evaluated in a diagnostic quantitative study trial utilizing radioactive $^{195m}$cisplatinum. The radiopharmaceutical was prepared using a $^{194}$Pt target and irradiation from neutron flux in a fission reactor (45,46). The preparation had an average specific activity of 0.8 mCi/mg of $^{195m}$cisplatinum. The study was approved by the institutional review board and radiation safety committee of Cooper Hospital University Medical Center for use of up to a 1.0 mCi dose of $^{195m}$cisplatinum, delivered intra-arterially. Institutional Review Board approved informed consent documents were signed by all patients participating in this study.

$^{195m}$Cisplatinum Imaging

Platinum-195m is a radionuclide with a physical half-life of 4.02 days. As it decays by isomeric transition it emits several photons imageable by scintillation camera. Six patients were imaged thirty minutes after administration of $^{195m}$cisplatinum (252–1011 $\mu$Ci) using a dual-head gamma camera system equipped with low-energy parallel-hole collimators. The camera was peaked at 76 keV with an energy window setting of 37%. This window setting maximized sensitivity without significantly degrading resolution. Tumors and normal liver containing Pt-195m uptake were identified and appropriate regions of interest drawn. The method used for quantitation of the radioactivity utilized conjugate view images (180° opposed anterior and posterior planar images). Prior to patient studies a phantom study was performed under fixed geometry to determine a correction factor for patient attenuation and scatter and a system calibration factor. The phantom consisted of a simulated tumor containing 277.5 $\mu$Ci of Pt-195m in an abdominal phantom filled with water to simulate patient attenuation and scatter. Analysis of the phantom study resulted in a correction factor which when applied to the patient conjugate view imaging data resulted in absolute activity in $\mu$Ci. The activities determined from the conjugate view counting technique were divided by the administered activity and multiplied by 100 to obtain the percent tumor uptakes. Tumor-to-normal liver ratios were determined from the various regions of interest.

Statistical methods: The log-rank procedure was used to test for any statistical differences in survival distribution between patient populations (47). Survival curves were generated by the Kaplan Meier technique (48). Each survival curve was plotted as a step function of the Kaplan-Meier estimates.

Results

Intra-arterial hepatic infusions were given to 67 patients with non-resectable hepatocellular carcinoma treated between July 1991 and September 1997. Clinical characteristics of these patients are provided in Table 1. All patients completed at least two monthly HAI cycles unless they had tumor progression of the primary or metastases or refused additional therapy.

For statistical analysis we examined patient factors such as AFP titer, the presence of extra-hepatic metastases and whether HAI CDDP was given as primary therapy or after prior treatment failure. Results of these patient groups will be presented according to the general outline in FIG. 1.

Overall survival was significantly different between the patients who were AFP (+) compared to patients who were AFP (−) (P=0.007) as determined by the log rank method. Survival curves comparing these two patient groups are shown in FIG. 2 and reveal that patients who were AFP (+) had a median survival of 10.3 months compared to 21.8 months for AFP (−) patients. Overall survival at one year was 45% for AFP (+) patients and 59% for AFP (−) patients.

The outcome of patients receiving HAI cisplatinum as their primary therapy was next studied. Survival of such patients with disease confined to their liver and no metastasis are shown in FIG. 3. Patients who were AFP (+) had a median survival of 12.0 months. For those patients who were AFP (−) median survival was 17.5 months.

Survival curves for patients with disease confined to their liver and who were referred after failing previous therapy are shown in FIG. 4. The median survival of AFP (+) patients was 17.3 months with 56% alive at one year. For those patients who were AFP (−) a median survival of 46.3 months was seen, with 75% alive at one year.

Table 2 reveals that patients who had extra-hepatic metastases had decreased survival. In patients with extra-hepatic metastases receiving HAI cisplatinum as primary therapy, those who were AFP (+) had a median survival of 7.1 months. Only a single patient who was AFP (−) had extra-hepatic metastases and she survived 21 months. Table 2 further reveals the survival data for patients with extra-hepatic metastases referred after prior treatment failure. Median survival of 8.9 months and 11.1 months was seen for those AFP (+) and AFP (−) patients, respectively.

The presence of chronic Hepatitis B or C was an important prognostic feature found in this study, with median survival of 10.7 months regardless of AFP status.

Toxicity of Treatment

All patients were assessable for analysis of toxicity. At 50 mg/m², HAI cisplatinum was well-tolerated, with patients repeatedly treated up to 60 months. Toxicity from HAI cisplatinum was hematologic as summarized in Table 3. As shown, 13% of patients experienced grade 3 or 4 leukopenia or thrombocytopenia. Combined leukopenia and thrombocytopenia of grade $\geq 3$ was seen in 19% of patients. No patient experienced radiation hepatitis, hearing impairment or renal toxicity and none required transfusions.

Diagnostic Quantitation Using $^{195m}$Cisplatinum

Because of a high response rate to intra-arterial cisplatinum compared to intravenous delivery a study was done to estimate whether there was a differential tumor uptake of cisplatinum. Patients were given similar tracer doses of $^{195m}$cisplatinum, first intravenously then by HAI. It was estimated that the maximum dose for this diagnostic quantitative trial would be 1.0 mCi, which would yield an estimated absorbed dose no greater than 5 centigray to the kidneys and therefore not cause toxicity. FIG. 5 shows a representative CT image of a patient (number 3, Table 4) prior to treatment. FIG. 6 is an example of his gamma camera study done the same day following the intra-arterial injection of 1.0 mCi $^{195}$Pt cisplatinum. Imaging studies demonstrate hyperconcentration of $^{195m}$cisplatinum in viable hepatoma. Table 4 summarizes the data for this diagnostic quantitative trial following HAI of $^{195m}$cisplatinum. As shown, the mean tumor uptake was 48.4% (range 34.2–55.4%) of the given activity and the mean ratio of tumor-to-liver uptake was 2.1 (range 1.6–2.4). In the six patients given HAI $^{195m}$cisplatinum no adverse events occurred.

DISCUSSION

Surgical resection is rarely achieved in hepatoma because it is multicentric at diagnosis and often with associated complications of chronic hepatitis and/or cirrhosis. In the 10 to 20% of patients who undergo resection, 20 to 100% will have cancer recur within the liver (6).

Palliative external radiation of the liver achieves amelioration of symptoms in more than 50% of patients (49). As radiation doses to the whole liver should not exceed 30 Gy, whole liver radiation by conventional external beam radiotherapy has not been extensively used in the treatment of hepatic cancer (19,50). Limited studies using conformal radiation allows increased dose delivery to the tumor while sparing normal tissue (18). Although doses in excess of 60 Gy can be given by the application of conformal radiotherapy techniques, the radiation volume to tumor and normal liver must be evaluated. Our prognostic rule was not to irradiate if normal liver was <50% of the total liver volume.

Systemic chemotherapy for non-resectable hepatoma is only modestly effective. Recent reviews suggested that no single drug or combination of drugs given intravenously leads to reproducible response rates of more than 25% or has significant effect on survival (51,52). Several controlled and uncontrolled studies have been performed with most of the major classes of cancer chemotherapy, given as single agents and in combination (53,54). For example, Cisplatin 75–80 mg/m$^2$ intravenously every 3 weeks results in objective tumor response rates of 6% to 17% (31,53,54). Agents such as 5-FU or mitomycin are inconsistently effective when given systemically (50). In a recent study where patients received alpha-interferon and systemic intravenous cisplatinum a median survival of 8.3 months was reported (26). These investigators described poor prognostic factors including the presence of portal vein thrombus, alkaline phosphatase $\geq 280$ U/L, total bilirubin $\geq 2.0$ mg/dl and serum triglyceride $\geq 155$ mg/dl. At present there is a paucity of evidence that systemic chemotherapy can consistently improve the overall survival of patients with HCC (27, 50–52,55). Table 5 illustrates selected treatment reports in advanced hepatoma.

In contrast to the results of systemic chemotherapy for regional or metastatic hepatoma, encouraging reports have appeared concerning regional chemotherapies for hepatoma confined to the liver. Higher response rates have generally been reported with intrahepatic arterial administration of chemotherapy with or without embolizing agents. Intra-arterial administration of dibutyrl cAMP and mitomycin C to 31 patients in Japan provided a median survival of a mere 5 months with 34% surviving to one year (56). In a recent prospective randomized study (14) there was no significant difference between intra-arterial $^{131}$I-lipiodol and chemoembolization as regards overall survival (38–42% at 1 year). In an Italian trial, patients received leucovorin, 5-fluorouracil and carboplatin by the intra-arterial route, followed by chemoembolization. A median survival of 11 months was reported (15).

It had been claimed that intra-arterial chemoembolization prolongs the survival of patients with hepatoma in uncontrolled trials (8,10) but a multicenter, randomized, controlled trial concluded that, although the treatment reduced tumor growth, it often caused episodes of liver decompensation and did not significantly improve survival (9). Moreover, no survival advantage was seen in a randomized trial comparing conservative management to intra-arterial chemoembolization (9).

The present study group achieved an overall median survival of 10.3 months.

More favorable results than those in this study have only been reported in a recent paper using octreotide (22). In this randomized, controlled study of 58 patients, octreotide was given subcutaneously or they received no active treatment. Of the 28 treated patients, serial AFP titers were reported for only 20 and of those, 3 patients (15%) lacked elevation in AFP titer. Median survival for those patients receiving octreotide was 13 months compared to 4 months in untreated controls. These results are similar to the present study with AFP positive patients achieving a median survival of 12 months.

Most patients in this study were treated with induction external beam hepatic radiotherapy with 50 mg/m$^2$ of intravenous cisplatinum, followed by HAI with cisplatinum. All patients were deemed not resectable by surgeons. (what are objective criteria?) Our treatment regimen of HAI involves 50 mg/m$^2$ cisplatinum infused at a rate of 1 mg/minute. The treatment is well tolerated and patients can usually be discharged after an overnight hospital stay required because of wound healing. In contrast to another study with increasing doses of cisplatinum (34) there did not appear to be a clinical limit to repeated infusions at 50 mg/m$^2$, with up to 60 cycles of cisplatinum delivered. The efforts to improve tumor remission by dose escalation has the result of increased toxicity and limited application with nine months of being administered (34). In our study we found that treatment could continue for years in responders and the most common toxicities experienced by patients with hepatoma receiving HAI cisplatinum were transient thrombocytopenia and leukopenia. No patient died of neither hematologic nor any other toxicity.

The rationale behind increased tumor remission using intra-arterial delivery of cisplatinum was observed. Using tracer quantities of $^{195m}$cisplatinum selective tumor uptake (i.e., 34–55% of administered dose) demonstrated first-pass kinetics were observed.

This study also shows the presence or absence of serum AFP to be a primary prognostic factor in patients with non resectable HCC as has been previously shown (16,57). Patients who were AFP (−) survived a median of 21 months compared with 10.3 months in patients who were AFP (+).

The presence of chronic Hepatitis B or C was a prognostic feature in this study, with median survival of 10.7 months regardless of AFP status. The status of hepatitis serology with survival was reported by Patt et al (39).

In summary, long term remission can be obtained in patients with non-resectable primary hepatoma using HAI infusion of 50 mg/m² cisplatinum. Using this treatment regimen, the median and overall survival for this group of patients deserves consideration as a standard initial treatment. The absence of severe hepatic or systemic toxicity despite repeated HAI suggests that the regimen described in this report may serve as a foundation against which randomized trials could be evaluated with other drug combinations. The use of $^{195m}$cisplatinum in tracer amounts demonstrates that intra-arterial infusion of cisplatinum selectively exposes the tumor to higher drug levels than can be achieved by the intravenous route.

References

1. Kew, M C. Hepatic tumors and cysts. In: Feldman M., Sleisenger M H, Scharschimdt B F, eds. Sleisenger & Fordtran's gastrointestinal and liver disease: pathology/diagnosis/management. 6$^{th}$ ed. Vol. 1. Philadelphia: W. B. Saunders, 1998:1364–87.

2. Godley P A, Sandier R S. Liver Cancer. In: Everhart J E, ed. Digestive diseases in the United States: epidemiology and impact. Washington, D.C.: Government Printing Office, 1994:227–41. (NIH publication no. 94-1447.)

3. El-Serag H B, Mason A C. Rising incidence of hepatocellular carcinoma in the United States. N Eng J Med 1999; 340:745–50.

4. McDermott W V, Cady B, Georgi B, Steele G Jr, Khettry U. Primary cancer of the liver. Evaluation, treatment and prognosis. Arch Surg 1989;124:552–4.

5. Johnson P J. Why can't we cure primary liver cancer? Eur J Cancer 1995;31A:1562–4.

6. Huguet C, Stipa F, Gavelli A. Primary hepatocellular cancer: Western experience. In: Blumgart, ed. Surgery of the liver and biliary tract. Vol 2. Edinburgh: Churchill Livingstone, 1994, Chap 92:1365–1369.

7. Okamura J, Monden M, Gotoh M, et al. Studies on the chemotherapy with 5-fluorouracil in transcatheter chemoembolization (TAE) treated patients with resectable or non-resectable hepatocellular carcinoma. Cancer Chemother Pharmacol 1989;23:S29–S32.

8. Nakamura H, Mitani T, Murakami T, et al. Five year survival after transcatheter chemoembolization for hepatocellular carcinoma. Cancer Chemother Pharmacol 1994;33 (suppl):S89–92.

9. Groupe D'Etude Et De Traitement Du Carcinome Hepatocellulaire. A comparison of lipiodol chemoembolization and conservation treatment for unresectable hepatocellular carcinoma. N Eng J Med 1995;332:1256–61.

10. Kasugai H, Kojima J, Tatsuta M, et al. Treatment of hepatocellular carcinoma by transcatheter arterial embolization combined with intra-arterial infusion of a mixture of cisplatin and ethiodized oil. Gastroenterology 1989;97:965–71.

11. Lin D, Liaw Y, Lee T, et al. Hepatic arterial embolization in patients with unresectable hepatocellular carcinoma: A randomized controlled trial. Gastroenterology 1988;94:453–56.

12. Venook A P, Stagg R J, Lewis B J, et al. Chemoembolization for hepatocellular carcinoma. J Clin Oncol 1990;8:1108–14.

13. Pelletier G, Roche A, Ink O. A randomized trial of hepatic arterial chemoembolization in patients with unresectable hepatocellular carcinoma. J Hepatology 1990;11:181–4.

14. Raoul J L, Guyader D, Bretagne J F, et al. Prospective randomized trial of chemoembolization versus intra-arterial injection of 131I-labeled-iodized oil in the treatment of hepatocellular carcinoma. Hepatology 1997;26(5):1156–61.

15. Colleoni M, Liessi G, Mastrapasqua G, et al. Intra-arterial chemotherapy followed by chemo-embolisation in unresectable hepatocellular carcinoma. Eur J Cancer 1997;33(1):56–60.

16. Order S E, Stillwagon G B, Klein J L, et al. Iodine 131 antiferritin: a new treatment modality in hepatoma: a Radiation Oncology Therapy Group Study. J Clin Oncol 1985;3:1573–82.

17. Stillwagon G B, Order S E, Guse C, Leibel S A, Asbell S O, Klein J L, Leichner P K. Prognostic factors in unresectable hepatocellular cancer:

18. Robertson J M, Lawrence T S, Dworzanin L M, Andrews J C, Walker S, Kessler M L, et al. Treatment of primary hepatobiliary cancer with conformal radiation therapy and regional chemotherapy. J Clin Oncol 1993;11:1286–1293.

19. Sherman D M, Weichelsbaum R, Order S E, Cloud L, Trey, Piro A J. Palliation of hepatic metastases. Cancer 1978;41:2013–2017.

20. Ettinger D S, Leichner P K, Siegelman S S, et al. Computed tomography assisted volumetric analysis of primary liver tumor as a response to therapy. Am J Clin Oncol 1985;8:413–418.

21. Epstein B E, Pajak T F, Haulk T L, Herpst J M, Order S E, Abrams R A. Metastatic nonresectable fibrolamellar hepatoma. Am J Clin Oncol 1999;22(1):22–28.

22. Kouroumalis E, Skordilis P, Thermos K, Vasilaki A, Moschandrea J, Manousos O N. Treatment of hepatocellular carcinoma with octreotide: a randomised controlled study. Gut 1998;42:442–447.

23. Mannesis E K, Giannoulis G, Zoumpoulis P, Vafiadou I, Hadjiyannis S G. Treatment of hepatocellular carcinoma with combined suppression and inhibition of sex hormones: a randomized, controlled trial. Hepatology 1995;21:1535–21.

24. Chao Y, Chan W-K, Huang Y-S, et al. Phase II study of flutamide in the treatment of hepatocellular carcinoma. Cancer 1996;77:635–9.

25. Cancer of the Liver Italian Programme Group. Tamoxifen in treatment of hepatocellular carcinoma: a randomised controlled trial. Lancet 1998;352:17–20.

26. Ji S K, Park N H, Choi H M, Kim Y W, Lee S H, Ahn S Y, Lee S U, Han B H, Park B C: Combined cisplatinum and alpha interferon therapy of advanced hepatocellular carcinoma. Korean J Intern Med 1996;11(1):58–68.

27. Moore D, Jr., Pazdur R. Systemic therapies for unresectable primary hepatic tumors. J Surg Oncol Suppl 1993;3:112–14.

28. Ravry J R, Omura G A, Bartolucci A A. Phase II evaluation of doxorubicin plus bleomycin in hepatocellular carcinoma: A Southeastern Cancer Study Group trial. Cancer Treat Rep 1984;68:1517–18.

29. Melia W M, Westaby D, Williams R. Diamminodichloride platinum (cisplatinum) in the treatment of hepatocellular carcinoma. Clin Oncol 1981;7:275–80.

30. Ravry J R, Omura G A, Bartolucci A A. Phase II evaluation of cisplatinum in advanced hepatocellular carcinoma and cholangiocarcinoma: A Southeastern Cancer Study Group trial. Cancer Treat Rep 1986;70:311–12.

31. Falkson G, Ryan L M, Johnson L A, et al. A randomized phase II study of mitoxantrone and cisplatin in patients with hepatocellular carcinoma: An ECOG study. Cancer 1987;60:2141–2145.

32. Bobbio-Pallavicini E, Porta C, Moroni M, et al. Epirubicin and etoposide combination chemotherapy to treat hepatocellular carcinoma patients: a phase II study. Eur J Cancer 1997;33(11):1784–8.

33. Blesing C H, Kerr D J. Intra-hepatic arterial drug delivery. J Drug Target 1996;3(5):341–7.

34. Carr B I. Escalating cisplatin doses by hepatic artery infusion (HAI) for advanced stage hepatocellular carcinoma (HCC). ASCO proceedings 1996;(15):198.

35. Carr B I. A controlled prospective randomized trial comparing intra-arterial (I/A) cisplatinum, doxorubicin and S/Q interferon alpha, with or without lipiodol for hepatocellular carcinoma (HCC). Hepatology 1992;16:60.

36. Onohara S, Kobayashi H, Itoh Y, et al. Intra-arterial cis-platinum infusion with sodium thiosulfate protection and angiotensin II induced hypertension for treatment of hepatocellular carcinoma. Acta Radiologica 1988;29:197–202.

37. Kajanti M, Rissanen P, Virkkunen P, et al Regional intra-arterial infusion of cisplatin in primary hepatocellular carcinoma. Cancer 1986;58:2386–88.

38. Shibata J, Fujiyama S, Sata T, et al. Hepatic arterial injection chemotherapy with cisplatin suspended in an oily lymphographic agent for hepatocellular carcinoma. Cancer 1989;64:1586–94.

39. Patt Y Z, Chamsangavej C, Yoffe B, et al. Hepatic arterial infusion of floxuridine, leucovorin, doxorubicin, and cisplatin for hepatocellular carcinoma: Effects of Hepatitis B and C viral infection on drug toxicity and patient survival. J Clin Oncol 1994;12:1204–11.

40. Mavlight G M, Patt Y Z, Haynie T P, Carrasco C H, Chamsangavej C, Wallace S. Differential tumor regression inpatients with bilobar hepatic metastases and dual arterial supply: Evidence supporting the advantage of intra-arterial over intravenous route of drug delivery. Selective Cancer Therapeutics 1989;5(1):37–45.

41. Pugh R N H, Murray-Lyon I M, Danson J L, Peitroni M C, Williams R. Transsection of esophagus for bleeding varices. Br J Surg 1973;60:646.

42. American Joint Committee on Cancer cancer staging manual, 5$^{th}$ edition, 1998, Lippincott-Raven Publishers, New York.

43. Yang N C, Leichner P K, Fishman E K, et al. CT volumetrics of primary cancers. J Comp Asst Tomogr 1986;10:621–628.

44. Late effects of normal tissues consensus conference. Int J Radiat Oncol Biol Phys 1992;31(5):1342–45.

45. Cole W C, Wolf W. Preparation and metabolism of a cisplatin/serum protein complex. Chem Biol Interactions 1980;30:223–35.

46. Anand D, Wolf W. A new, semi-automated system for the micro-scale synthesis of ($^{195m}$Pt)cisplatin suitable for clinical studies. Appl Radiat Isot 1992;43(6):809–14.

47. Mantel N. Evaluation of survival data and two new rank order statistics arising in its consideration. Cancer Chemotherapy Reports 1966;5:163–70;.

48. Kaplan E L, Meier P. Nonparametric estimation from incomplete observations. JASA 1958;53:457–81.

49. DiBisceglie A M, Rustgi V K, Hoofnagle J H, Dusheiko G M, Lotze M T. NIH Conference: hepatocellular cancer. Ann Intern Med 1988;108:390–401.

50. Friedman M A. Primary hepatocellular cancer: present results and future prospects. Int J Radiat Oncol Biol Phys 1983;9:1841–50.

51. Lee, Y-T N. Systemic and regional treatment of primary carcinoma of the liver. Cancer Treat Rev 1977; 4:195–212.

52. Nerenstone S R, Ihde D C, Friedman M A. Clinical trials in hepatocellular carcinoma: Current status and future directions. Cancer Treat Rev 1988;15:1–31.

53. Okada S, Okazaki N, Nose H, Shimada Y, Yoshimori M, Aoki K. A phase 2 study of cisplatin in patients with hepatocellular carcinoma. Oncology 1993;50:22–26.

54. Falkson G, Lavin P, Moertel C G, Pretorius F J, Carbone P P. Chemotherapy studies in primary liver cancer a prospective randomized clinical trial. Cancer 1978;42:2149–57.

55. Luporini G, Labianca R, Pancera G. Medical treatment of hepatocellular carcinoma. J Surg Oncol 1993;Suppl 3:115–18.

56. Kusano S, Katayama M, Uematsu M, et al. Intraarterial infusion of dibutryl cyclic adenosine monophosphate plus mitomycin C for unresectable hepatocellular carcinoma: long-term survival and response to tumor growth inhibition. Acad Radiol 1995;2(4):286–92.

57. Nomura F, Ohnishi K, Tanabe Y. Clinical features and prognosis of hepatocellular carcinoma with reference to serum alpha-fetoprotein levels, analysis of 606 patients. Cancer 1989;64:1700–07.

TABLE 1

| Patient Characteristics | | |
|---|---|---|
| Total number | 67 | |
| Gender | | |
| Male | 52 | (78%) |
| Female | 15 | (22%) |
| Age, years | | |
| Median | 59 | |
| Range | 24–88 | |
| Ethnicity | | |
| Caucasian | 56 | (84%) |
| African-American | 7 | (10%) |
| Asian | 4 | ( 6%) |
| Karnosky performance status | | |
| 90–100% | 56 | (84%) |
| 70–80% | 11 | (16%) |
| Ascites present | 16 | (24%) |
| Elevated bilirubin ($\geq$1.5) | 13 | (19%) |
| Elevated SGOT | 57 | (85%) |
| Elevated alkaline phosphatase | 46 | (69%) |
| Hepatitis B antigen positive | 15 | (22%) |
| Hepatitis C antigen positive | 14 | (21%) |
| Elevated alpha-fetoprotein | | |
| ($\geq$11 ng/ml, AFP positive) | 45 | (67%) |
| 11–1,000 | 18 | (40%) |
| 1,000–10,000 | 7 | (16%) |
| >10,000 | 20 | (44%) |
| Tumor volume (cm$^3$) | | |
| $\leq$250 | 2 | ( 3%) |
| 251–500 | 12 | (18%) |
| 501–1,000 | 21 | (31%) |
| >1,000 | 32 | (47%) |
| Median tumor volume | 915 cm$^3$ | |
| (range) | (146–4464 cm$^3$) | |

TABLE 1-continued

Patient Characteristics

| | | |
|---|---|---|
| Modified Child-Pugh Classification | | |
| Group A | 50 | (75%) |
| Group B | 17 | (25%) |
| TNM classification | | |
| II | 7 | (10%) |
| III | 11 | (16%) |
| IVA | 32 | (48%) |
| IVB | 16 | (24%) |

TABLE 2

Survival of patients with extra-hepatic metastases

| Use of HAI-CDDP | AFP status | No. of patients | Median survival (months) |
|---|---|---|---|
| As primary therapy | elevated | 10 | 7.1 |
| | not elevated | 1 | 21.0 (one patient) |
| After prior treatment failure | elevated | 3 | 8.9 |
| | not elevated | 3 | 11.1 |

TABLE 3

RTOG Grade 3 or 4 toxicities (% of patients)

| Toxicity | Grade 3 | Grade 4 | Total |
|---|---|---|---|
| Leukopenia | 10 | 3 | 13 |
| Thrombocytopenia | 8 | 5 | 13 |
| Combined leukopenia and thrombocytopenia* | 14 | 5 | 19 |

*Combined toxicity is the maximum of the leukopenia and thrombocytopenia grades for each patient.

TABLE 4

$^{195m}$Cisplatinum uptake by hepatic intra-arterial infusion

| Patient | Administered activity ($\mu$Ci) | Tumor activity ($\mu$Ci) | Tumor uptake (%) | Tumor-to-liver uptake ratio |
|---|---|---|---|---|
| 1 | 252 | 140 | 55.4 | 1.6 |
| 2 | 1011 | 501 | 49.6 | 2.3 |
| 3 | 1000 | 528 | 52.8 | 2.4 |
| 4 | 1011 | 489 | 48.3 | 2.1 |
| 5 | 1003 | 343 | 34.2 | 2.3 |
| 6 | 1000 | 503 | 50.3 | 2.0 |

FIGURE LEGENDS

Figure one: Overview of patient groups. The number of patients in each group are shown in parentheses. Median survival in months is presented for each group.

Figure two: Survival of patients with elevated or non-elevated AFP titer.

Figure three: Survival of patients without extra-hepatic metastases receiving HAI CDDP as primary treatment.

Figure four: Survival of patients without extra-hepatic metastases receiving HAI CDDP after prior treatment failures.

Figure five: Abdominal CT scan of a patient (number 3, Table 4) with biopsy-proven hepatoma showing extensive tumor in the right lobe of the liver.

Figure six: Gamma camera study of patient (number 3, Table 4) done same day following intra-arterial injection of 1.0 mCi $^{195}$Pt cisplatinum. This imaging study demonstrates hyperconcentration of $^{195m}$cisplatinum in viable hepatoma.

What is claimed is:

1. A method of treating cancer comprising administering a therapeutically effective amount of radioactive cisplatin.

2. The method of claim 1 wherein the amount of cisplatin is about 10 mCi to about 75 mCi.

3. The method of claim 1 wherein the cisplatin is administered intra-arterially.

4. The method of claim 1 wherein the cisplatin is $195^m$ cisplatin.

5. A method of interrupting DNA metabolism in a cell by administering a therapeutically effective amount of radioactive cisplatin.

* * * * *

UNITED STATES PATENT AND TRADEMARK OFFICE
CERTIFICATE OF CORRECTION

PATENT NO.   : 6,074,626
DATED        : June 13, 2000
INVENTOR(S)  : Stanley E. Order It is certified that error appears in the above-identified patent and that said Letters Patent is hereby corrected as shown below:

The patent specification and abstract of the invention should appear as shown in the attached pages.

UNITED STATES PATENT AND TRADEMARK OFFICE
CERTIFICATE OF CORRECTION

PATENT NO. : 6,074,626
DATED : June 13, 2000
INVENTOR(S) : Stanley E. Order

It is certified that error appears in the above-identified patent and that said Letters Patent is hereby corrected as shown below:

RELATED APPLICATIONS

This application claims the benefit of the filing date of provisional application serial number 60/078,818 filed on March 20, 1998, the entire disclosure of which is incorporated by reference herein.

BACKGROUND OF THE INVENTION

Hepatocellular cancer that is non-resectable has had a median survival of six months when treated. A variety of chemotherapeutic agents have been given intravenously, with less-than-realistic results. During the course of investigations in hepatocellular cancer. Isurprisingly discovered that intra-arterial cisplatin at 50 mg./m$^2$ caused a 50% remission in 28 patients; and, recently, in 67 patients, a 50% response. Thus, 95 patients have had a 50% remission, with median survival extended one year to 46 months depending on the classification of the tumor. In addition to these findings, the median survival rate for the worst group of hepatomas (AFP+positive) was one year greater than the six months reported from the other therapeutic regimens.

In order to discern why intra-arterial cisplatin was superior to intravenous, I created 195$^m$ cisplatin, and studied the same patient intravenously and intra-arterially. When the drug was given intravenously, less than five percent deposited in the tumor. Then the drug was given intra-arterially, 35 to 40 percent of the drug deposited in the tumor, as witnessed by scintigraphic scans. The cisplatin that binds on the hepatoma apparently stays there for a persistent period of time and interrupts DNA metabolism. The use of intravenous cisplatin has had less than a five-percent response rate, and the arterial route is 50 percent or greater.

Having studied the diagnostic distribution of 195$^m$ cisplatin, I realized that the possibility of treating cancer with a radioactive cisplatin exists.

I have been engaged in Phase 1 dose escalation study in which 10 mCi of radioactivity, approximately 10 mg of the drug, are substituted for the cold drug in the infusion of the liver. The dose is escalated as long as there is no signification hematologic toxicity. The maximum dose we presently give of 50 mg/m$^2$ on an average person would be about 70 to 75 mg. The procedure would take the 195$^m$ cisplatin and substitute it for the cold, and the patient would get both the cold cisplatin and the radioactive cisplatin. Cisplatin is also a radiation sensitizer, and, as such, the drug should amplify the therapeutic results from the radiolabeling.

The benefit to the patient would be that the non-radioactive form and the radioactive form would still behave as the drug cisplatin, since it is created radioactive by neutron bombardment and not by chemistry alteration or linkage.

Cisplatin has been used diagnostically in a variety of tumors where its direct infusion is part of the pharmacacokinetics. Therapy with 195$^m$ cisplatin would have use in hematoma, bladder and brain tumors, but prior to the present invention has never been proposed for this use.

UNITED STATES PATENT AND TRADEMARK OFFICE
CERTIFICATE OF CORRECTION

PATENT NO. : 6,074,626
DATED : June 13, 2000
INVENTOR(S) : Stanley E. Order

It is certified that error appears in the above-identified patent and that said Letters Patent is hereby corrected as shown below:

A dosage range of approximately 10mCi to 75mCi or more, depending upon the size of the tumor, may be given in accordance in this invention for all types of solid tumor cancers and not limited to hepatomas.

Without further elaboration, the foregoing so fully illustrates my invention that others may adapt and use the invention accordingly.

ABSTRACT OF THE INVENTION

A method of treating cancer comprising administering a therapeutically effective amount of cisplatin.

Signed and Sealed this

Fourteenth Day of May, 2002

*Attest:*

*Attesting Officer*

JAMES E. ROGAN
*Director of the United States Patent and Trademark Office*